(12) United States Patent
Tan et al.

(10) Patent No.: US 6,617,462 B1
(45) Date of Patent: Sep. 9, 2003

(54) BITHIENYLNAPHTHALENE-AND BIS(3,4-ETHYLENEDIOXYTHIENYL) NAPHTHALENE-BASED MONOMERS AND POLYMERS

(75) Inventors: Loon-Seng Tan, Centerville, OH (US); Balasubramanian Sankaran, Dayton, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 09/973,177

(22) Filed: Oct. 9, 2001

Related U.S. Application Data

(60) Division of application No. 09/497,034, filed on Feb. 2, 2000, now Pat. No. 6,359,149, which is a continuation-in-part of application No. 09/255,689, filed on Feb. 23, 1999, now Pat. No. 6,291,621.

(51) Int. Cl.[7] .............................................. C07D 409/00

(52) U.S. Cl. ............................. 549/29; 549/42; 549/59; 549/78; 549/80

(58) Field of Search ............................. 549/59, 42, 29, 549/78, 80

(56) References Cited

U.S. PATENT DOCUMENTS 6,291,621 B1    9/2001   Tan et al.

OTHER PUBLICATIONS

Sankaran et al. [Polymer Preprints (American Chemical Society, Division of Polymer Chemistry), 39(1), 157–158 (1998)].*
B. Sankaran, L–S Tan, Structure–Property Relationships of Bis(Tehylenedioxythienylnaphthalene) Systems, Polymer Preprints, vol. 40, No. 1, Mar. 1999, pp. 189–190.

* cited by examiner

Primary Examiner—Kelechi Egwim
(74) Attorney, Agent, or Firm—Charles E. Bricker; Thomas L. Kundert

(57) ABSTRACT

Electropolymerizable monomers of the formulas

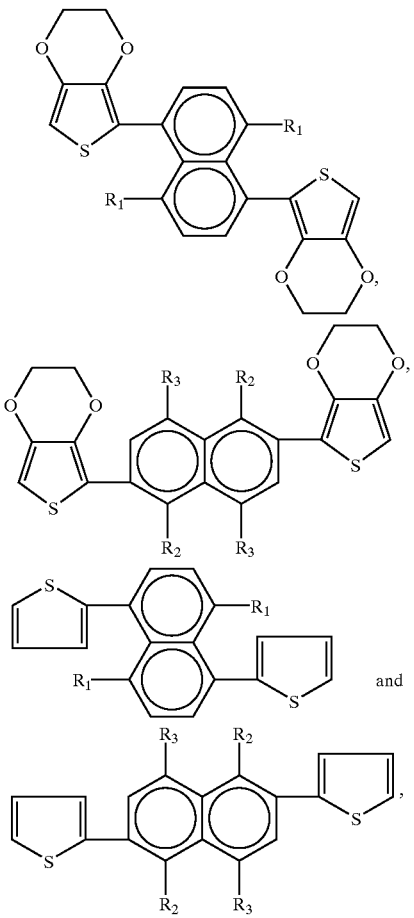

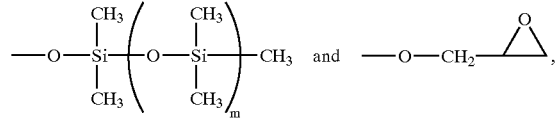

wherein $R_1$, $R_2$ and $R_3$ are selected from the group consisting of —H, —O(CH$_2$)$_n$CH$_3$, wherein n has a value of 0 to 11 and m has a value of 1 to 4, and wherein no more than one of $R_2$ and $R_3$ is —H. Also provided are polymers resulting from the electropolymerization of these monomers.

3 Claims, No Drawings

BITHIENYLNAPHTHALENE- AND BIS(3,4-ETHYLENEDIOXYTHIENYL) NAPHTHALENE-BASED MONOMERS AND POLYMERS

This is a division of Ser. No. 09/497,034, filed Feb. 2, 2000, now U.S. Pat. No. 6,359,149, issued Mar. 19, 2002, which is a continuation-in-part of Ser. No. 09/255,689, filed Feb. 23, 1999, now U.S. Pat. No. 6,291,621, issued Sep. 18, 2001.

RIGHTS OF THE GOVERNMENT

The invention described herein may be manufactured and used by or for the Government of the United States for all governmental purposes without the payment of any royalty.

BACKGROUND OF THE INVENTION

The present invention relates to conducting polymers and their use as electrodes in various devices, and, in particular, to certain bithienylnaphthalene- and bis(3,4-ethylenedioxythienyl)naphthalene-based monomers and polymers.

It is known that conjugated polymeric systems derived from regio-selective synthetic processes that preclude or minimize structural defects have shown, among other properties, much higher conductivity. A version of this approach is illustrated by the design and preparation of symmetrical conjugated monomers like bis(heterocycle-arylene) monomers, which upon electropolymerization, have led to polymers with minimal side reactions. Since these monomers and derived polymers are highly conjugated, they exhibit interesting and potentially useful luminescence characteristics. Most of the literature in poly (bis-heterocycle-arylenes) has focused on benzene as the arylene system. We have found that naphthalene as the arylene part provides more sites to modify the molecular structures of the monomers, and in turn, more control of the electronic properties of the derived polymers to satisfy the bulk property requirements.

It is an object of the present invention to provide novel monomers for the production of thin films and coatings useful in electrochromic applications.

It is another object of the present invention to provide polymers prepared by polymerization of these monomers.

Other objects, aspects and advantages of the present invention will be apparent to those skilled in the art from a reading of the following detailed disclosure of the invention.

SUMMARY OF THE INVENTION

In accordance with the present invention there are provided novel, electropolymerizable monomers of the formulae:

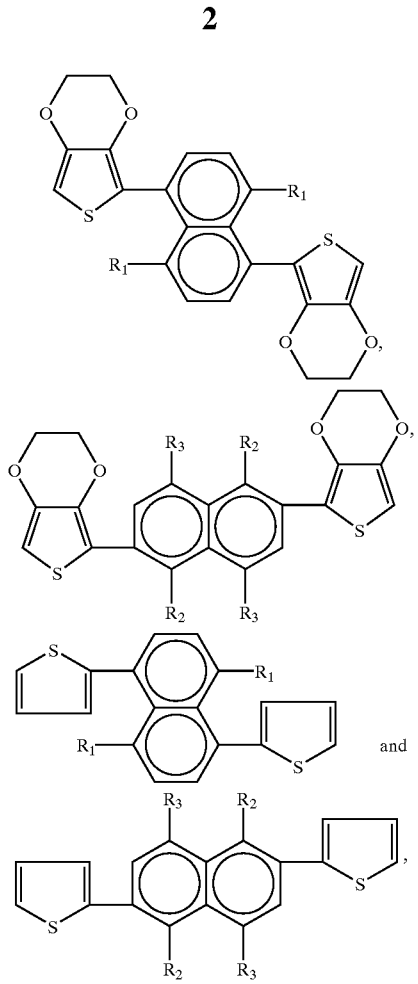

wherein $R_1$, $R_2$ and $R_3$ are selected from the group consisting of —H, —O(CH$_2$)$_n$CH$_3$,

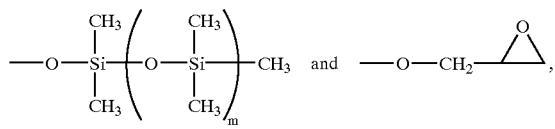

wherein n has a value of 0 to 11 and m has a value of 1 to 4, and wherein no more than one of $R_2$ and $R_3$ is —H.

These monomers are synthesized by the palladium-catalyzed coupling reaction of 2-(tributylstannyl)thiophene or 2-(tributylstannyl)ethylenedioxythiophene with a naphthyl ditriflate or naphthyl dibromide as shown in the examples which follow. The coupling reaction works well in dioxane or toluene at reflux with tetrakis-(triphenylphosphine)palladium(O), Pd(PPh$_3$)$_4$.

These monomers are preferably electrochemically polymerized. Electrochemical polymerization of the above-described monomers can be carried out according to the methods generally employed for electrochemical polymerization of thiophene, pyrrole, and the like. The electrochemical copolymerization is carried out by cyclic voltammetry, by subjecting a mixture of monomer, solvent and electrolyte to one of the following conditions: (a) setting the potentiostat at a constant electrical potential where the monomer is optimally oxidized; (b) setting the potentiostat at a constant current value; or (c) repeated scanning between the redox potentials of the monomers. Typically, all three conditions are tested for a new monomer in order to select one as the optimal condition for achieving electropolymerized polymer films with the required stability and thickness. If the oxidation-reduction cycle can be repeated several times and the polymer film deposited on the electrode exhibits reproducible cyclic voltammetric (current-voltage) characteristics, it is then deemed to be electrochemically stable and well-behaved.

Within the context of the implementation of the process in accordance with the invention, the electrochemical reactions are advantageously carried out at the surface of an electrode. By measuring the current delivered during the reaction, the electrode effectively makes it possible to monitor the progress of the polymerization reaction (for example the thickness of the polymer formed) or the progress of subsequent reactions carried out on the copolymer.

The resulting polymers have the structures

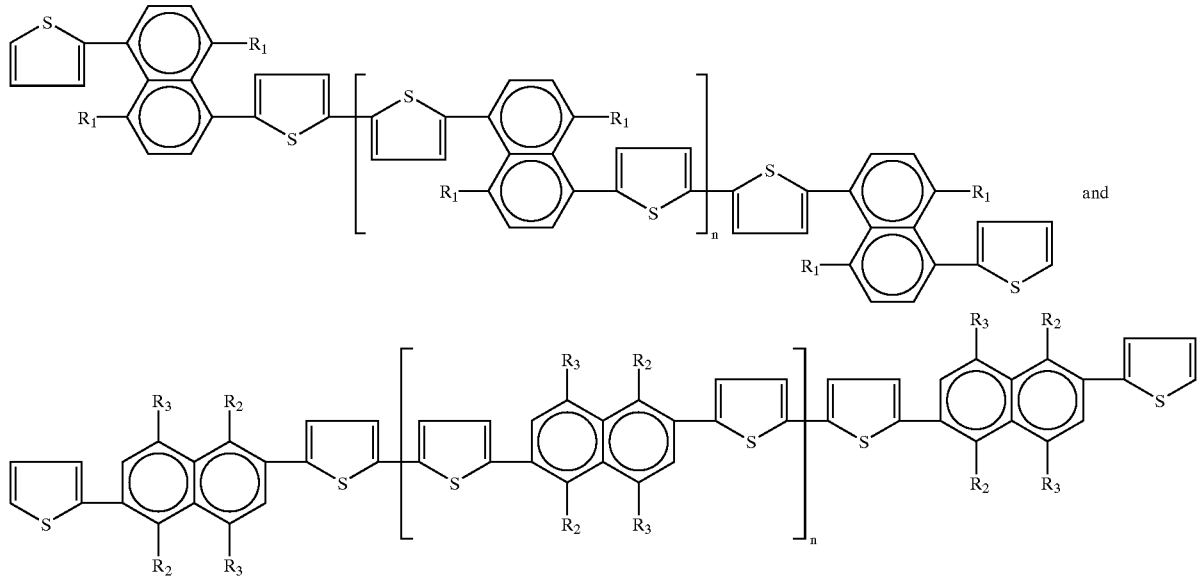

wherein $R_1$, $R_2$ and $R_3$ are as previously defined and n is an integer indicating the degree of polymerization and having a value of at least 1. The ethylenedioxythiophene-containing polymers have similar structures.

The following examples illustrate the invention:

EXAMPLE 1

1,5-Bistrifluoromethanesulfonatenaphthalene (1,5-BTFN)

1,5-Naphthalendiol (6.00 g., 0.038 mol.) dissolved in 60 mL of pyridine was cooled to 0° C. under nitrogen atmosphere. Previously chilled trifluoromethanesulfonic acid anhydride (23.28 g., 0.083 mol.) was added dropwise from a syringe over a period of 15 minutes. After the reaction mixture had been magnetically stirred for 5 hours at 0° C., it was allowed to slowly warm up to the room temperature. It was then poured into 100 mL of diethyl ether, washed with water and dilute aqueous HCl via a separatory funnel. The organic layer was subsequently dried and concentrated to afford an off-white solid. The product was obtained as white crystals after recrystallization from diethyl ether. Yield: 87%. M.p.114.5–115.5° C. Anal. Calcd for $C_{12}H_6F_6$: C, 33.97%; H, 1.43%; S, 15.11%. Found: C, 34.17%; H, 1.32%; S, 15.14%. Mass Spectrum: 424.06 ($M^+$). $^1$H-NMR ($CDCl_3$; □ in ppm): 8.15 (d, 2H), 7.62 (dd, 2H), 7.7 (d, 2H). $^{13}$C-NMR ($CDCl_3$; □ in ppm): 145.4, 127.9, 127.3, 121.5, 121.1, 119.4, 116.3.

EXAMPLE 2

2,6-Bistrifluoromethanesulfonatenaphthalene (2,6-BTFN)

2,6-Naphthalendiol (2.60 g., 0.016 mol.) dissolved in 60 mL of pyridine was cooled to 0° C. under nitrogen atmo- The solvents which can be used in the present invention may be either aqueous or nonaqueous, although a solution of the aforesaid electrolyte in a nonaqueous organic solvent is preferred. The organic solvents used herein are preferably aprotic and have high dielectric constants. For example, ethers, ketones, nitriles, amines, amides, sulfur compounds, phosphoric ester compounds, phosphorous ester compounds, boric ester compounds, chlorinated hydrocarbons, esters, carbonates, nitro compounds and the like can be employed. Of these, ethers, ketones, nitriles, phosphoric ester compounds, phosphorous ester compounds, boric ester compounds, chlorinated hydrocarbons and carbonates are preferred. Specific examples of suitable solvents include tetrahydrofuran, 2-methyltetrahydrofuran, 1,4-dioxane, acetonitrile, proprionitrile, 4-methyl-2-pentanone, butyronitrile, valeronitrile, benzonitrile, 1,2-dichloroethane, .gamma.-butyrolactone, valerolactone, dimethoxyethane, methylformate, propylene carbonate, ethylene carbonate, dimethylformamide, dimethyl sulfoxide, ethyl phosphate, methyl phosphate, ethyl phosphite, methyl phosphite, 3-methylsulfolane, etc. Among these, nitriles and carbonates are especially preferred in order to increase the response speed. These organic solvents may be used alone or in combination.

Specific examples of electrolyte which can be used in the present invention include tetraphenylarsonium chloride, tetraphenylphosphonium chloride, tetra(n-butyl)ammonium bromide, lithium bromide, tetra(n-butyl)ammonium hexafluorophosphate, and tetra(n-butyl)ammonium perchlorate (TBAP). These examples are merely illustrative and not limiting.

sphere. Previously chilled trifluoromethanesulfonic acid anhydride (10.00 g., 0.035 mol.) was added dropwise from a syringe over a period of 15 minutes. After the reaction mixture had been magnetically stirred for a few hours at 0° C., ice-bath was removed and stirring was continued overnight. The resultant mixture was then poured into 100 mL of diethyl ether, washed with water and dilute aqueous HCl via a separatory funnel. The organic layer was dried over $MgSO_4$ and subsequently concentrated on a rotary evaporator to afford the crude product as a white solid. The desired product was obtained as yellowish white crystals after recrystallization from $CH_2Cl_2$. Yield 78%. M.p. 82.5–84.5° C. Anal. Calcd. for $C_{12}H_6F_6$: C, 33.98%; H, 1.42%; S, 15.12%; F, 26.87%. Found: C, 33.97%; H, 1.13%; S, 15.10%; F, 25.37%. Mass spectrum: 424.19 (M+). $^1$H-NMR ($CDCl_3$; □ in ppm): 7.97 (d, 2H; J=9 Hz), 7.82 (d, 2H; J=3 Hz), 7.48 (dd, 2H; J=9 Hz, 2 Hz). $^{13}$C-NMR ($CDCl_3$; □ in ppm.): 147.8, 132.4, 130.8, 121.4, 121.1, 119.4, 116.3.

EXAMPLE 3

1,5-Bis(2-thienyl)naphthalene (1,5-BTN)

Into a 250 mL, round-bottomed flask containing 100 mL of anhydrous 1,4-dioxane was added 3 g. (0.0071 mol.) of 1,5-bistrifluoromethanesulfonatenaphthalene, 12.20 g. (0.028 mol.) of 2-(tributylstannyl)thiophene (Aldrich) and 1.80 g. of LiCl under argon atmosphere. $Pd(PPh_3)_4$ (70 mg) was transferred into the reaction flask using a Schlenk tube under argon and the reaction mixture was refluxed for 18 h. The dark reaction mixture was cooled, mixed with 4 g. of KF, and stirred for another 8 hrs. Finally, $CH_2Cl_2$ (100 mL) was added to the reaction mixture which was briefly stirred and then filtered through a cake of Celite. The organic layer of the filtrate was separated, washed with water, diluted aqueous HCl, and dried over $MgSO_4$. A crude solid was obtained after the solvent had been stripped off via a rotary evaporator. White crystalline solid was obtained after recrystallization from $CH_2Cl_2/CH_3OH$ (40:60). Yield: 83%. M.p. 193–195° C. Anal. Calcd. for $C_{18}H_{12}S_2$: C, 73.94%; H, 4.14%; S, 21.93%. Found: C, 72.36%; H, 3.99%; S, 20.92%. Mass Spectrum: 292.22 (M+). $^1$H-NMR ($CDCl_3$; □ in ppm): 7.18 (dd, 2H), 7.24 (dd, 2H), 7.42 (dd, 2H), 7.48 (d, 2H), 7.59(dd, 2H), 8.2 (d, 2H). $^{13}$C-NMR ($CDCl_3$; □ in ppm): 141.7, 132.7, 132.4, 128.4, 127.5, 127.2, 126.2, 125.7, 125.6.

EXAMPLE 4

2,6-Bis(2-thienyl)naphthalene (2,6-BTN)

Into a flask containing 40 mL of anhydrous 1,4-dioxane was added 1 g. (0.0024 mol.) of 2,6-bistrifluoromethanesulfonatenaphthalene, 3.52 g (0.0094 mol.) of 2-(tributylstannyl)thiophene and 0.450 g. of LiCl under argon atmosphere. 70 mg. of $Pd(PPh_3)_4$ was transferred into the reaction flask using a Schlenk tube under argon and the reaction mixture was refluxed for 4 hrs. The dark reaction mixture was cooled, added with 4 g. of KF, and stirred for another 8 hrs. Finally, $CH_2Cl_2$ (100 mL) was added to the reaction mixture which was briefly stirred and then filtered through a cake of Celite. The organic layer of the filtrate was separated, washed with water, diluted aqueous HCl, and dried over $MgSO_4$. A crude solid was obtained after the solvent had been stripped off via a rotary evaporator. Glistening yellow solid was obtained after recrystallization from $CH_2Cl_2/CH_3OH$ (40:60). Yield 58%. M.p. 256–258° C. Anal. Calcd.$C_{18}H_{12}S_2$: C, 73.94%; H, 4.14%; S, 21.93%. Found: C, 74.29%; H, 4.07%; S, 22.51%. Mass spectrum: 291.87 (M+). $^1$H-NMR ($CDCl_3$; □ in ppm): 7.14 (dd, 2H), 7.34 (dd, 2H), 7.47 (d, 2H), 7.77 (d, 2H), 7.87 (d, 2H), 8.03 (s, 2H).

EXAMPLE 5

1,5-Dimethoxy-4,8-bis(2-thienyl)naphthalene (4,8-BTDMN)

1,5-Dimethoxy-4,8-dibromonaphthalene (1.19 g., 0.0034 mol.) and 2-(tributylstannyl)thiophene (3.85 g., 0.0103 mol.) were dissolved in 100 mL dry toluene in argon atmosphere. $Pd(PPh_3)_4$ (100 mg.) was introduced into the reaction flask using a Schlenk tube under argon. The resultant mixture was subsequently refluxed for 18 hrs. The brownish black solution was cooled and poured into 300 mL of petroleum ether to afford crude yellow solid. Upon recrystallization from $CH_2Cl_2$:petroleum ether (1:5), the desired product was obtained as a light yellow solid. Yield: 81%. M.p. 216–218° C. Anal. Calcd. for $C_{20}H_{16}O_2S_2$: C, 68.15%; H, 4.58%; S, 18.19%. Found: C, 67.64%; H, 4.48%; S, 17.49%. Mass spectrum: 351.75 (M+). $^1$H-NMR ($CDCl_3$; □ in ppm): 3.59 (s, 3H), 6.81 (d, 2H), 6.89 (d, 2H), 7.00 (dd, 2H), 7.26 (dd, 2H), 7.38 (d, 2H). $^{13}$ C-NMR ($CDCl_3$; □ in ppm): 55.6, 106.5, 123.1, 123.5, 125, 125.5, 126.1, 131.1, 147.5, 156.8.

EXAMPLE 6

1,5-Dimethoxy-2,6-bis(2-thienyl)naphthalene (2,6-BTDMN)

1,5-Dimethoxy-2,6-dibromonaphthalene (1.00 g., 0.0029 mol.) and 2-(tributylstannyl)thiophene (4.314 g., 0.0116 mol.) were dissolved in 100 mL dry toluene in argon atmosphere. $Pd(PPh_3)_4$ (100 mg.) was introduced into the reaction flask using a Schlenk tube under argon. The resultant mixture was subsequently refluxed for 18 hrs. The brownish black solution was cooled and poured into 300 mL of petroleum ether to afford crude yellow solid. Upon recrystallization from $CH_2Cl_2$:petroleum ether (1:5), the desired product was obtained as a light yellow solid. Yield: 95%. M.p. 225–228° C. Anal. Calcd. for $C_{20}H_{16}O_2S_2$: C, 68.15%; H, 4.58%; S, 18.19%. Found: C, 67.98%; H, 4.53%; S, 18.03%. Mass spectrum: 351.84 (M+). $^1$H-NMR ($CDCl_3$; □ in ppm): 3.88 (s, 3H), 7.16 (dd, 2H), 7.43 (dd, 2H), 7.63 (dd, 2H), 7.83 (d, 2H, 9 Hz), 7.96 (d, 2H, 9 Hz). $^{13}$C-NMR ($CDCl_3$; □ in ppm): 61.3, 119.0, 123.2, 125.7, 126.5, 126.6, 126.9, 129.2, 138.9, 152.1.

EXAMPLE 7

1,4,5,8-Tetramethoxy-2,6-bis(2-thienyl)naphthalene (2,6-BTTMN)

1,4,5,8-Tetramethoxy-2,6-dibromonaphthalene (7.80 g., 0.019 mol.) and 2-(tributylstannyl)thiophene (18.00 g., 0.048 mol.) were dissolved in 200 mL dry toluene under argon atmosphere. $Pd(PPh_3)_4$ (100 mg.) was introduced into the reaction flask using a Schlenk tube under argon. The resultant mixture was subsequently refluxed for 18 hrs. The brownish black solution was cooled and poured into 500 mL of petroleum ether to afford crude yellow solid. Upon recrystallization from $CH_2Cl_2$/petroleum ether (1:3) the desired product was obtained as a light yellow solid. Yield: 96%. M.p. 233.5–237° C. Anal. Calcd. for $C_{22}H_{20}O_4S_2$: C, 64.06%; H, 4.89%; S, 15.54%. Found: C, 64.12%; H, 4.90%; S, 15.12%. Mass spectrum: 411.84 (M+). $^1$H-NMR ($CDCl_3$; □ in ppm.): 3.73 (s, 3H), 4.05 (s, 3H), 7.13 (dd, 2H), 7.19 (s, 2H), 7.41 (dd, 2H), 7.59(dd, 2H,). $^{13}$C-NMR (CDCl$_3$; □ in ppm.): 56.7, 61.7, 107.5, 122.5, 124.4, 125.7, 126.6, 126.9, 139.1, 146.5, 152.5.

EXAMPLE 8

2-Tributylstannyltin-3,4-ethylenedioxythiophene 3,4-Ethylenedioxythiophene (25 g., 0.176 mol.) in 100 ml of ethyl ether (anhy.) was cooled to −78° C. under an argon atmosphere and 77 ml of 2.5 M n-butyllithium (0.1935 mol.) was dripped slowly with constant stirring. After 2 hours at this temperature, the reaction mixture was treated with tri-n-butyltin chloride (85.9 g., 0.264 mol.) with the aid of a hypodermic syringe. The final reaction mixture was allowed to warm to room temperature with continuous stirring over a period of 18 h. Then, 50 ml of 5% KF solution was added and the reaction mixture was stirred for 2 more hours. The organic layer of the mixture was separated, dried, filtered, and the solvent was stripped off to yield 74 g. of 2-tributylstannyl-3,4-ethylenedioxythiophene. The isolated product was used in the preparation of the examples 9–13 without any further purification.

EXAMPLE 9

1,5-Bis(2-(3,4-ethylenedioxylthienyl)naphthalene (1, 5-BEDOTN)

Into a 3-necked 250 ml round-bottomed flask equipped with a reflux condenser, a gas inlet/outlet adaptor and glass stopper, was added 1,5-bistrifluoromethanesulfonatenaphthalene (2 g., 0.0047 mol.), 2-tributyltinethylenedioxythiophene (4.47 g., 0.0104 mol.) and LiCl (0.5 g.) and 100 mL 1,4-dioxane (anhydrous and degassed), under argon atmosphere. Pd(PPh$_3$)$_4$ (55 mg.) was transferred into the reaction flask using a Schlenk tube under argon and the reaction mixture was refluxed for 18 hrs. The dark reaction mixture was allowed to cool to room temperature and 3 g. of KF was added to it. The final mixture was stirred at room temperature for 8 hrs. After addition of CH$_2$Cl$_2$ (100 mL), the mixture was stirred and filtered through a layer of Celite. With the aid of a separatory funnel, the organic layer was washed with water, then diluted HCl, dried over anhydrous MgSO$_4$. Off-white crude product was obtained after the solvent had been removed via rotary evaporation. Repetitive recrystallization of the crude product from CH$_2$Cl$_2$: CH$_3$OH (v/v 40: 60) yielded white crystalline solid. M.P.=299–303° C., Yield 74%. Anal. Calcd.: C, 64.71%; H, 3.94%; S, 15.67%. Found: C, 63.07%; H, 3.63%; S, 15.38%. Mass Spectrum; M$^+$ (m/e =407.97). $^1$H-NMR (CDCl$_3$; δ in ppm): 8.04 (dd, 2H), 7.55 (dd, 2H), 7.52 (dd, 2H), 6.48 (s, 2H), 4.27 (m, 4H), 4.25 (m, 4H).

EXAMPLE 10

2,6-Bis(2-(3,4-ethylenedioxythienyl)naphthalene (2, 6-BEDOTN)

Into a 3-necked 100 ml round-bottomed flask equipped with a reflux condenser, a gas inlet/outlet adaptor and glass stopper, was added 2,6-bistrifluoromethanesulfonatenaphthalene (0.5 g., 0.00118 mol.), 2-tributyltinethylenedioxythiophene (2.04 g. 0.0047 mol.) and LiCl (0.45 g.) and 40 mL 1,4-dioxane (anhydrous and degassed), under argon atmosphere. Pd(PPh$_3$)$_4$ (70 mg.) was transferred into the reaction flask using a Schlenk tube under argon and the reaction mixture was refluxed for 12 hrs. The dark reaction mixture was allowed to cool to room temperature. 100 mL of 5% aqueous KF and 100 mL of CH$_2$Cl$_2$ was added to it. The final mixture was stirred at room temperature for 2 hrs and then filtered through a layer of Celite. With the aid of a separatory funnel, the organic layer was washed with water, then diluted HCl, dried over anhydrous MgSO$_4$. Yellowish-green, amorphous solid was obtained after the solvent had been removed via rotary evaporation. Recrystallization of the crude product from CH$_2$Cl$_2$: CH$_3$OH (v/v 40:60) yielded glistening yellow solid. M.P.=208–211° C., Yield 85%. Anal. Calcd.: C, 64.71%; H, 3.94%; S, 15.67%. Found: C, 63.07%; H, 3.63%; S, 15.38%. Mass Spectrum; M$^+$ (m/e=408.22). $^1$H-NMR (CDCl$_3$; δ in ppm): 8.13 (s, 2H ), 7.81 (dd, 4H), 6.34 (s, 2H ), 4.36 (m, 4H ). 4.28 (m, 4H) $^{13}$C-NMR (CDCl$_3$; δ in ppm): 142.4, 138.5, 132.4, 130.5, 128.3, 129.9, 124.1, 117.7, 97.9, 64.8, 64.5.

EXAMPLE 11

1,5-Dimethoxy-4,8-bis(2-(3,4-ethylenedioxythienyl) naphthalene (4,8-BEDOTDMN)

1,5-Dimethoxy-4,8-dibromonaphthalene (11.96 g., 0.0278 mol.) and 2-tributylethylenedioxythiophene (3.86 g., 0.011 mol.) were dissolved in 100 mL dry toluene in argon atmosphere. This was followed by the transfer of Pd(PPh$_3$)$_4$ (100 mg.) into the reaction flask using a Schlenk tube under argon. The resultant mixture was refluxed for 18 hrs. The brownish black solution was allowed to cool to room temperature and then poured into 300 mL of petroleum ether to afford a brown solid The crude product was subsequently recrystallized from CH$_2$Cl$_2$: petroleum ether (v/v 1:5) to yield a white, amorphous solid. M.P.=308–313° C., Yield 53%. Anal. Calcd: C, 61.52%; H, 4.33%; S, 13.69%. Found: C, 61.75%; H, 4.10%; S, 13.45%. Mass Spectrum: M$^+$ (m/e=468.25). $^1$H-NMR (CDCl$_3$, δ in ppm): 3.32 (s, 3H), 3.35 (s,3H), 4.05 (dd, 4H), 4.07 (dd, 4H), 6.4 (s, 2H), 6.9 (d, 2H), 7.3 (d, 2H). $^{13}$C-NMR (CDCl$_3$; δ in ppm): 55.7, 64.04, 64.2, 119.07, 119.48, 125.5, 137, 140.4, 156.5.

EXAMPLE 12

1,5-Dimethoxy-2,6-bis(2-ethylenedioxythienyl) naphthalene (2,6-BEDOTDMN)

1,5-Dimethoxy-2,6-dibromonaphthalene (1 g. 0.0029 mol.) and an excess of 2-tributyltinethylenedioxythiophene (7.67 g., 0.0173 mol.) were dissolved in 100 mL dry toluene in an argon atmosphere. This was followed by the transfer of Pd(PPh$_3$)$_4$ (100 mg.) into the reaction flask using a Schlenk tube under argon. The resultant mixture was refluxed for 18 hrs. The brownish black solution was allowed to cool to room temperature and then poured into 300 mL of petroleum ether to afford a yellow solid The crude product was subsequently recrystallized from CH$_2$Cl$_2$: petroleum ether (v/v 1:5) to yield a light greenish yellow solid. M.P.= 298–303° C., Yield: 44%. Anal. Calcd: C, 61.53%; H, 4.30%; S, 13.66%. Found: C, 60.89%; H, 4.17%; S, 12.93%. Mass Spectrum: M$^+$ (m/e=468.09). $^1$H-NMR (CDCl$_3$, δ in ppm): 3.87 (s, 6H), 4.28 (dd,4H), 4.35 (dd, 6H), 6.46 (s, 2H), 7.90 (d, 2H, 9 Hz), 8.15 (d, 2H, 9 Hz). $^{13}$C-NMR (CDCl$_3$; δ in ppm): 61.54, 64.33, 64.85, 100.10, 112.7, 118.2, 121.8, 126.9, 128.4, 139.1, 141.3, 151.9.

EXAMPLE 13

1,4,5,8-Tetramethoxy-2,6-Bis(2-ethylenedioxythienyl)naphthalene (2,6-BEDOTTMN)

1,4,5,8-Tetramethoxy-2,6-dibromonaphthalene (5.03 g., 0.0124 mol.) and an excess of 2-tributyltinethylenedioxythiophene (25 g., 0.058 mol.) were dissolved in 200 mL dry toluene in an argon atmosphere. This was followed by the transfer of $Pd(PPh_3)_4$ (100 mg.) into the reaction flask using a Schlenk tube under argon. The resultant mixture was refluxed for 18 hrs. The brownish black solution was allowed to cool to room temperature and then poured into 500 mL of petroleum ether to afford a greenish yellow solid The crude product was subsequently recrystallized from $CH_2Cl_2$:petroleum ether (v/v 1:3) to yield a greenish yellow solid. M.P.=300–303° C., Yield: 74%. Anal. Calcd: C, 59.08%; H, 4.58%; S, 12.21%; O, 24.21C%. Found: C, 58.36%; H, 4.56%; S, 10.86%; O 23.48%. Mass Spectrum: $M^+$ (m/e=528.12). $^1$H-NMR ($CDCl_3$, δ in ppm): 3.73 (s, 6H), 4.0 (s, 6H), 4.27 (dd, 4H), 4.29 (dd, 4H), 6.44 (s, 2H), 7.68 (s, 2H,). $^{13}$C-NMR ($CDCl_3$; δ in ppm): 56.62, 61.97, 62.06, 64.93, 100.42, 107.87, 113.2, 121.52, 122.91, 138.95, 141.05, 146.38, 151.85.

EXAMPLE 14

General Procedure for Electropolymerization

Electropolymerizaton was carried out with a Parr 273 Potentiostat/Galvanostat instrument using electrochemical software. The cell consists of gold button electrode as the working electrode, $Ag/Ag^+$ in 0.1 M $TBAP/CH_3CN$ as the reference electrode, and platinum sheet as the counter electrode. Typically, 10 mM of the monomer, dissolved in 0.1 M $TBAP/50:50$ (v/v) of $CH_2Cl_{2/CH3}CN$ was used for polymerization studies. The cell, with the electrometer was enclosed in a chamber under positive pressure of $N_2$. A standard electrolyte/solvent cyclic voltammetry curve was obtained and the electrolyte was found to be stable from −1.0 to 1.1 V. All the monomers were well characterized and their purity were checked by HPLC before being used in the electropolymerization experiments. The monomers were electrochemically polymerized onto a gold button electrode. These polymers were rinsed in the solution of electrolyte solvent and were used to study the redox behavior in monomer free electrolyte solution.

Monomer potentials, polymer potentials and potentials for deposition of polymers are summarized in the following table:

TABLE

| Compound | Monomer potential (V) | | Polymer potential (V) | | Potential for polymer deposition (V) |
|---|---|---|---|---|---|
| | $E_a$ | $E_{c,p}^a$ | $E_{a,p}^b$ | $E_{c,p}^c$ | |
| 2,6-BTN | 0.73 | 0.43 | 0.45 | 0.51 | 0.90 |
| 1,5-BTN | 0.95 | 0.02 | 0.59 | −0.03 | 1.10 |
| 2,6-BTDMN | 0.71 | 0.41 | 0.45 | 0.45 | 0.85 |
| 4,8-BTDMN | 0.72 | 0.56 | 0.43 | 0.51 | 1.10 |
| 2,6-BTTMN | 0.59 | 0.51 & 0.35 | polymer soluble in solvent used | | |
| 2,6-BEDOTN | 0.40 | 0.20 | 0.37 | 0.20 | 0.6 |
| 1,5-BEDOTN | 0.75 | — | 0.45 | −0.15 | 0.9 |
| 2,6-BEDOTDMN | 0.52 | — | 0.34 | 0.31 | 0.8 |
| 4,8-BEDOTDMN | 0.42 | 0.48 | 0.53 | 0.52 | 1.0 |
| 2,6-BEDOTTMN | 0.36 | 0.22 | polymer soluble in solvent used | | |

Notes:
<sup>a</sup>$E_{c,p}$ = Monomer cathodic peak potential
<sup>b</sup>$E_{a,p}$ = Polymer oxidation potential
<sup>c</sup>$E_{c,p}$ = Polymer reduction peak potential The monomers of this invention are useful in the fabrication of electrochromic and electrically conducting materials. The thin polymer films resulting from electropolymerization of these monomers are useful as electrochromic materials in electronic display devices, electrochromic windows and devices which require changes in color and degree of light transmittance.

Various modifications may be made to the invention as described without departing from the spirit of the invention or the scope of the appended claims.

We claim:
1. 1,5-dimethoxy-4,8-bis(2-thienyl)naphthalene.
2. 1,5-dimethoxy-2,6-bis(2-thienyl)naphthalene.
3. 1,4,5,8-tetramethoxy-2,6-bis(2-thienyl)naphthalene.

* * * * *